United States Patent [19]

Kirst et al.

[11] 4,341,771

[45] Jul. 27, 1982

[54] METHOD OF CONTROLLING PASTEURELLA INFECTIONS

[75] Inventors: Herbert A. Kirst, Indianapolis; Earl E. Ose, Greenfield, both of Ind.

[73] Assignee: Eli Lilly and Company, Indianapolis, Ind.

[21] Appl. No.: 255,577

[22] Filed: Apr. 20, 1981

[51] Int. Cl.³ .................... A61K 31/71; A61K 31/70
[52] U.S. Cl. .................................. 424/181; 424/180
[58] Field of Search ............................... 424/180, 181

[56] References Cited

U.S. PATENT DOCUMENTS

| | | | |
|---|---|---|---|
| 3,178,341 | 4/1965 | Hamill et al. | 167/65 |
| 3,326,759 | 6/1967 | Hamill et al. | 167/65 |
| 3,344,024 | 9/1967 | Whaley et al. | 167/65 |
| 3,459,853 | 8/1969 | Gorman et al. | 424/121 |
| 3,769,273 | 10/1973 | Massey | 260/210 |
| 4,234,690 | 11/1980 | Weinstein et al. | 435/119 |
| 4,252,898 | 2/1981 | Nash et al. | 435/76 |

OTHER PUBLICATIONS

Fuzi et al.–Chem. Abst. vol. 92 (1980), p. 122,584p, and vol. 85 (1976), p. 751a.

K. Fujisawa et al., "Studies on Cirramycin $A_1$. II Biological Activity of Cirramycin $A_1$," *J. Antibiotics 22(2)*, 65–70 (1969).

H. Tsukiura et al., "Studies on Cirramycin $A_1$. IV Derivatives of Cirramycin $A_1$," *J. Antibiotics 22(3)*, 100–105 (1969).

T. Furumai et al., "Macrolide Antibiotics M-4365 Produced by *Micromonospora*. I. Taxonomy, Production, Isolation, Characterization and Properties," *J. Antibiotics 30*, 443–449 (1977).

T. Yamaguchi et al., "Macrolide Antibiotics M-4365 Produced by *Micromonospora* III, *In Vitro* Antimicrobial Activity of Antibiotic M-4365 $G_2$ (De-epoxy Rosamicin)", *J. Antibiotics 31*, 433–440 (1978).

*Primary Examiner*—Sam Rosen
*Attorney, Agent, or Firm*—Nancy J. Harrison; Arthur R. Whale

[57] ABSTRACT

Method of controlling Pasteurella infections which comprises administering to an infected or susceptible warm-blooded animal an effective amount of 5-O-mycaminosyl tylonolide or a pharmaceutically acceptable acid addition salt thereof.

7 Claims, No Drawings

METHOD OF CONTROLLING PASTEURELLA INFECTIONS

SUMMARY OF THE INVENTION

This invention relates to a method of controlling Pasteurella infections. In particular, this invention relates to the method of controlling Pasteurella infections which comprises administering to an infected or susceptible warm-blooded animal 5-O-mycaminosyl tylonolide (OMT) or a pharmaceutically acceptable acid addition salt of OMT.

Pasteurella infections cause serious economic losses in animals. Pasteurellosis, which is a respiratory disease in sheep, cattle and pigs, and fowl cholera are examples of severe diseases in which Pasteurella species are either the primary, or important secondary, etiological agents. *P. multocida* and *P. haemolytica* are the agents implicated in these diseases.

DETAILED DESCRIPTION OF THE INVENTION

We have discovered that OMT and the acid addition salts of OMT exhibit unexpectedly high antibacterial activity against certain gram-negative bacteria. More particularly, we have discovered that these compounds are effective in vivo as well as in vitro againt Pasteurella species such as *P. multocida* and *P. haemolytica*.

OMT was described by Marvin Gorman and Robert B. Morin in U.S. Pat. No. 3,459,853, issued Aug. 5, 1969. Gorman and Morin taught that OMT inhibited gram-positive bacteria.

The structure of OMT is shown in formula 1:

OMT can be prepared by hydrolysis of tylosin, desmycosin, macrocin or lactenocin under mildly acidic conditions as described in U.S. Pat. No. 3,459,853. Another method of preparing OMT is described by Richard H. Baltz, Gene M. Wild, and Eugene T. Seno in their copending application entitled DEMYCINOSYL-TYLOSIN AND PROCESS FOR ITS PRODUCTION, Ser. No. 156,854, filed June 12, 1980. This method comprises preparing OMT by mild acid hydrolysis of 23-demycinosyltylosin (DMT). The structure of DMT is shown in formula 2:

DMT is prepared by fermentation of *Streptomyces fradiae* NRRL 12170 under submerged aerobic conditions until a substantial level of antibiotic activity is produced. DMT can be extracted from basified broth filtrate with polar organic solvents and can be further purified by extraction, chromatography, and/or crystallization. The DMT-producing strain of *Streptomyces fradiae* has been deposited and made part of the stock culture collection of the Northern Regional Research Center, Agricultural Research, North Central Region, 1815 North University St., Peoria, Ill., 61604, from which it is available to the public under the accession number NRRL 12170.

OMT is prepared from DMT by mild acid hydrolysis. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating DMT with a mild acid solution for a time sufficient to effect removal of the mycarosyl group to give OMT.

Alternatively, and sometimes preferably, OMT can be prepared by treating DMT in the fermentation broth in which it is produced, using mild acidic conditions as described above for a time sufficient to convert the DMT to OMT. OMT thus prepared can be isolated from the fermentation broth using techniques known in the art.

In carrying out the method of this invention, an effective amount of OMT or a pharmaceutically acceptable acid addition salt of OMT is administered parenterally to an infected or susceptible warm-blooded animal. The does which is effective to control Pasteurella infections will vary with the severity of the infection and the age, weight, and condition of the animal. The total dose required for several days protection will generally, however, be in the range of from about 10 to about 400 mg/kg and preferably will be in the range of from about 25 to about 350 mg/kg. Protection for several days can be provided by a single injection; the length of protection will depend upon the dose given. For example, a single injection of 77 mg/kg of OMT provided protection in calves for about seven days. Alternatively, the total dose can be divided into smaller doses given at intervals. For example, a dose of 25 mg/kg of OMT administered once daily for five days provided protection in calves. Obviously, other suitable dosage regimens can be constructed.

The compounds of this invention may be formulated for parenteral administration by methods recognized in the veterinary pharmaceutical art. Effective injectable compositions containing these compounds may be in either suspension or solution form. In the preparation of suitable formulations it will be recognized that, in general, the water solubility of OMT acid addition salts is greater than that of OMT base. Similarly, OMT base is more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The compounds of this invention exhibit unexpectedly high antibacterial activity against Pasteurella species both in vitro and in vivo. For example, in the conventional broth-dilution assay, the mean minimal inhibitory concentration (MIC) of OMT against six isolates of *P. multocida* was 4.6 mcg/ml, and the mean MIC of OMT against six isolates of *P. haemolytica* was 6.0 mcg/ml.

Examples one through five illustrate the useful in vivo activity of OMT. In each of these examples OMT (free base) was administered in an aqueous propylene glycol solution, and non-medicated water and feed were provided to the animals ad libitum.

EXAMPLE 1

OMT for the Treatment of Pasteurellosis in Mice

OMT was evaluated in mice by subcutaneous injection given either one or one and four hours post challenge of the mice with *Pasteurella multocida* (0.1 ml of a $10^{-5}$ dilution of a tryptose broth culture of a bovine isolate). Mortality was evaluated for the following seven days. The results are summarized in Table I.

TABLE I

| Treatment of Pasteurellosis in Mice with OMT | | |
|---|---|---|
| Dosage | Replicate | No. Died/No. Treated |
| OMT 50 mg/kg × 2 | 1 | 0/5 |
|  | 2 | 0/5 |
| OMT 50 mg/kg × 1 | 1 | 0/5 |

TABLE I-continued

| Treatment of Pasteurellosis in Mice with OMT | | |
|---|---|---|
| Dosage | Replicate | No. Died/No. Treated |
|  | 2 | 0/5 |
| OMT 25 mg/kg × 2 | 1 | 0/5 |
|  | 2 | 0/5 |
| OMT 25 mg/kg × 1 | 1 | 4/5 |
|  | 2 | 3/5 |
| OMT 10 mg/kg × 2 | 1 | 1/5 |
|  | 2 | 0/5 |
| OMT 10 mg/kg × 1 | 1 | 4/5 |
|  | 2 | 3/5 |
| OMT 1 mg/kg × 2 | 1 | 4/5 |
|  | 2 | 3/5 |
| Tylosin tartrate | 1 | 4/5 |
| 50 mg/kg × 2 | 2 | 5/5 |
| Nonmedicated, | 1 | 5/5 |
| Infected | 2 | 5/5 |
| Controls | | |

EXAMPLE 2

OMT for the Treatment of Pasteurellosis in Chicks

OMT was evaluated in one-day-old chicks at a dosage of 30 mg/kg by subcutaneous injection given one and four hours post challenge of the chicks with *Pasteurella multocida* (0.1 ml of a 20-hour tryptose broth culture of an avian *P. multocida* given subcutaneously). None of the ten treated chicks died during the following five-day observation period. All ten nonmedicated infected chicks died within 24 hours of Pasteurella challenge.

EXAMPLE 3

Treatment of Induced Bacterial Pneumonia in Pigs with OMT

Tables II through V summarize the results from two experiments in pigs in which OMT was compared with tylosin base (TYLAN ® 200) at dosage levels of 25 mg/kg and 8.8 mg/kg. Drugs were injected subcutaneously twice daily for five days as a treatment for induced bacterial pneumonia. In each experiment, OMT and tylosin treatment was initiated one day following challenge of the pigs with the pneumonic lung tissue suspension.

The animals for these experiments were purchased as healthy feeder pigs from a farm in central Indiana. The pigs were transported to the research facility, individually weighed, identified, and divided into replicates based on mean bodyweight.

In each experiment one group was treated with OMT, one group was treated with tylosin, and one group was not treated. The experiments were terminated after 28 days.

The system by which bacterial swine pneumonia was induced was conducted in two phases. The initial step involved the oral administration of a known number of *Ascaris suum* ova to each pig. Five to ten days later, when migration of ascaris larvae should have been creating damage to the lung tissue, a suspension of pneumonic swine lung, containing viable *Pasteurella multocida* and *Corynebacterium pyogenes*, was instilled intranasally into each animal.

In the first step, a standardized suspension of *A. suum* ova, prepared by the method of L. C. Costello [see *J. Parasit.* 47, 24 (1961)], was pipetted into the mouth of each pig. The number of ova given per animal in each trial was 150,000. This number was higher than the number normally used due to loss of ova viability.

Six to eight days later each pig was given 10 ml of pneumonics lung tissue suspension, administered intranasally.

Pneumonic lung tissue was obtained from swine experiencing acute pneumonia. Pneumonic lung tissue was maintained at −60° C. until needed.

A tissue suspension for challenge inoculation was prepared using a Waring blender to homogenize one part thawed pneumonic tissue and five parts cold physiologic saline. The pneumonic lung homogenate contained approximately $10^6$ to $10^7$ viable *P. multocida*/ml and $10^7$ to $10^8$ viable *C. pyogenes*/ml. Prior to intranasal administration of this suspension, the pigs were subjected to forced exercise to induce rapid respiration.

Individual animal body weight were recorded periodically during each experiment. Mortality was recorded daily. All pigs that died, and surviving pigs that were sacrificed at the end of each trail, were examined for pulmonary lesions and/or the cause of death. Sections of pneumonic tissue were cultured for bacteria, using defibrinated equine blood agar plates with incubations in aerobic and carbon dioxide atmospheres at 37° C.

TABLE II

Mortality, Weight Gain, Gross Lung Lesions and Reisolation of Pathogens

| Treatment | Replicate | No. Died/ No. in Group | Weight Data (Lbs.) Initial | Final |
|---|---|---|---|---|
| OMT, 8.8 mg/kg × 2, 5 days | 1 | 0/8 | 28.9 | 48.8 |
| | 2 | 0/8 | 29.3 | 49.6 |
| Mean or Total | | 0/16 | 29.1 | 49.2 |
| | | | Gain[a] 20.1 lbs. | |
| TYLAN® 200, 8.8 mg/kg × 2, 5 days | 1 | 0/8 | 28.8 | 52.9 |
| | 2 | 0/8 | 29.3 | 53.5 |
| Mean or Total | | 0/16 | 29.05 | 53.2 |
| | | | Gain[a] 24.1 lbs. | |
| Infected, Nonmedicated Controls | 1 | 2/8 | 28.9 | 50.3 |
| | 2 | 0/8 | 28.8 | 43.3 |
| Mean or Total | | 2/16 | 28.85 | 46.8 |
| | | | Gain[a] 18.0 lbs. | |

[a] Average gain per pig within each group during the 28-day test period.

| Treatment | Replicate | No. with Bacterial Pneumonic Lung Lesions/ No. Examined | Reisolation of Pathogens From Lung Tissue P. multocida | C. pyogenes |
|---|---|---|---|---|
| OMT, 8.8 mg/kg × 2, 5 days | 1 | 4/8 | 3/8 | 2/8 |
| | 2 | 3/8 | 3/8 | 0/8 |
| Total | | 7/16 | 6/16 | 2/16 |
| TYLAN® 200, 8.8 mg/kg × 2, 5 days | 1 | 1/8 | 1/8 | 0/8 |
| | 2 | 5/8 | 5/8 | 1/8 |
| Total | | 6/16 | 6/16 | 1/16 |
| Infected, Nonmedicated Controls | 1 | 6/8 | 5/7[b] | 4/7[b] |
| | 2 | 6/8 | 6/8 | 6/8 |
| Total | | 12/16 | 11/15 | 10/15 |

[b] Lung from one pig not cultured due to autolysis.

TABLE III

Severity of Bacterial Pneumonic Lung Lesions

| Treatment | Negative | Slight (1-5%) | Moderate (6-20%) | Severe (>20%) |
|---|---|---|---|---|
| OMT, 8.8 mg/kg × 2 5 days | 9 | 4 | 2 | 1 |
| TYLAN® 200 8.8 mg/kg × 2, 5 days | 10 | 4 | 2 | 0 |
| Infected, Nonmedicated Controls | 4 | 2 | 4 | 6 |

TABLE IV

Mortality, Weight Gain, Gross Lung Lesions and Reisolation of Pathogens

| Treatment | Replicate | No. Died/ No. in Group | Weight Data (Lbs.) Initial | Final |
|---|---|---|---|---|
| OMT, 25 mg/kg × 2, 5 days | 1 | 0/8 | 20.5 | 35.4 |
| | 2 | 0/8 | 20.0 | 35.1 |
| Mean or Total | | 0/16 | 20.3 | 35.3 |
| | | | Gain[a] 15.0 lbs. | |
| TYLAN® 200, 25 mg/kg × 2, 5 days | 1 | 0/8 | 20.3 | 35.2 |
| | 2 | 0/8 | 20.1 | 38.1 |
| Mean or Total | | 0/16 | 20.2 | 36.7 |
| | | | Gain[a] 16.5 lbs. | |
| Infected, Nonmedicated Controls | 1 | 5/8 | 20.2 | 30.7 |
| | 2 | 3/8 | 20.0 | 30.8 |
| Mean or Total | | 8/16 | 20.1 | 30.7 |
| | | | Gain[a] 10.6 lbs. | |

[a] Average gain per pig within each group during the 28-day test period.

| Treatment | Replicate | No. with Bacterial Pneumonic Lung Lesions/ No. Examined | Reisolation of Pathogens From Lung Tissue P. multocida | C. pyogenes |
|---|---|---|---|---|
| OMT, 25 mg/kg × 2, 5 days | 1 | 0/8 | 0/8 | 1/8 |
| | 2 | 0/8 | 0/8 | 0/8 |
| Total | | 0/16 | 0/16 | 1/16 |
| TYLAN® 200, 25 mg/kg × 2, 5 days | 1 | 0/8 | 0/8 | 0/8 |
| | 2 | 0/8 | 0/8 | 1/8 |
| Total | | 0/16 | 0/16 | 1/16 |
| Infected, Nonmedicated Controls | 1 | 8/8 | 7/8 | 7/8 |
| | 2 | 8/8 | 7/8 | 5/8 |
| Total | | 16/16 | 14/16 | 12/16 |

TABLE V

Incidence of Clinical Signs of Pneumonia

| Treatment | Sign | No. with Clinical Signs/No. Examined Days Post Pneumonic Lung Tissue Challenge 4 | 9 | 12 |
|---|---|---|---|---|
| OMT, 25 mg/kg × 2, 5 days | Nasal Discharge | 0/16 | 1/16 | 1/16 |
| | Cough | 0/16 | 2/16 | 0/16 |
| | Labored Breathing | 0/16 | 9/16 | 16/16 |
| TYLAN® 200 25 mg/kg × 2, 5 days | Nasal Discharge | 0/16 | 3/16 | 4/16 |
| | Cough | 1/16 | 1/16 | 1/16 |
| | Labored Breathing | 0/16 | 14/16 | 16/16 |
| Infected, Nonmedicated Controls | Nasal Discharge | 0/16 | 3/13 | 4/9 |
| | Cough | 6/16 | 6/13 | 4/9 |
| | Labored Breathing | 1/16 | 13/13 | 9/9 |

OMT was effective as a treatment in both experiments. It was more effective at the 25 mg/kg level, based upon reduction of pneumonic lung lesions, reduction in the number of pigs with lungs from which pathogenic bacteria could be isolated, reduction in the number of pigs with clinical signs and a reduction in body temperature.

EXAMPLE 4

Treatment of Pneumonia in Calves with OMT

OMT was evaluated in calves for the treatment of naturally occurring pneumonia. Calves were purchased and transported to Lilly Research Laboratories, Greenfield, Indiana. The calves were weighed, bled, identified with eartags and allotted into pens soon after arrival. Rectal temperatures were taken and clinical observations were made daily.

Calves were put on test at the first signs of respiratory disease which included ocular and nasal discharges, pyrexia and/or depression.

Treated calves were injected intramuscularly with OMT in an aqueous propylene glycol vehicle. The treatment doses evaluated were 12.5 mg/kg and 25 mg/kg once a day for five days. Control calves were treated with placebo. There were 10 calves per group. Calves that died were examined at necropsy for lesions indicative of pneumonia. Surviving calves were killed seven days after the last treatment and examined for lesions at necropsy.

The temperature averages of the calves in the 25 mg/kg- and 12.5 mg/kg-treatment groups were lowered to normal by the second day of treatment. In comparison, the average temperatures of nonmedicated controls remained above 40° C. (104° F.) for 10 days after they were put on test. Scours and ocular discharge were reduced in the treated calves at both OMT dose levels. Six of ten placebo-treated calves died, whereas only two of ten in each of the OMT-treated groups died. At necropsy extensive pathologic lesions in lung tissue were indicative of a severe pneumonia in the calves that died during the trial.

Ureaplasma sp. was isolated from lung tissue of calves treated with placebo and 12.5 mg OMT/kg but was not isolated from calves treated with 25 mg OMT/kg. The method of controlling Ureaplasma infections with OMT is discussed in our copending patent application entitled METHOD OF CONTROLLING UREAPLASMA INFECTIONS, Ser. No. 255,575, filed herewith this even date.

OMT was effective in the treatment of calf pneumonia by reducing severity of clinical signs and lowering mortality. Additionally, treatment with 25 mg/kg of OMT was effective against Ureaplasma sp.

EXAMPLE 5

Prevention of Pneumonia in Calves with OMT

OMT was evaluated in calves for the prevention and control of naturally occurring pneumonia. Calves were purchased and transported to Lilly Research Laboratories, Greenfield, Ind. Soon after arrival the calves were weighed, bled, identified with eartags and allotted into pens. There were 19 calves in the OMT-treated group and 19 calves in the nontreated control group.

OMT was prepared as an injectable solution in an aqueous propylene glycol vehicle. The treated calves were each injected subcutaneously with 35 mg/lb (77 mg/kg) of OMT within a day after arrival. At this dose and route of administration, the drug was expected, based on blood level studies, to persist for seven days in the treated calves. The calves were each retreated with the same dose seven days later. Rectal temperatures were taken and clinical observations were made daily. Calves that died were examined at necropsy for lesions indicative of pneumonia.

During the 14-day observation period following the first injection, the average temperatures were lower in treated calves than in the non-medicated controls. Treated calves had less severe nasal and ocular discharges and less severe scours. Calves on treatment also appeared more alert and in better condition than the controls. The cumulative mortality for the first 14 days was as follows:

| Group* | CUMULATIVE MORTALITY RATE Days of Test | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Control | 0 | 0 | 0 | 1 | 3 | 5 | 5 | 5 | 9 | 11 | 13 | 14 | 14 | 15 |
| OMT | 0 | 0 | 0 | 0 | 0 | 0 | 0 | 0 | 0 | 0 | 0 | 0 | 2 | 3 |

*19 Calves per Group

The mortality data indicated that treatment with OMT was very effective in preventing death of calves due to a severe pneumonia. The naturally occurring pneumonia in these calves was judged to be severe based upon the high mortality rate of non-medicated controls. Additionally, all of the calves that died were examined at necropsy; of these, 14 of the 15 control calves and the 3 treated calves had extensive pathologic lesions indicative of severe pneumonia.

EXAMPLE 6

Preparation of OMT from DMT

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| $CaCO_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| $(NH_4)_2HPO_4$ | 0.04 |
| $CaCO_3$ | 0.2 |
| Soybean oil (crude) | 3.0 |

| Ingredient | Amount (%) |
| --- | --- |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vetetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
| --- | --- |
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. The product thus obtained can be recrystallized from acetone-water.

D. Preparation of OMT

DMT, prepared as described in Section C, is dissolved in a dilute hydrochloric acid solution (final pH 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is evaporated under vacuum to give OMT.

EXAMPLE 7

Alternate Preparation of OMT from DMT

OMT is prepared from DMT by treating the DMT in the fermentation broth in which it is produced with mild acid as described in Section D of Example 6. Isolation of the OMT is accomplished by a procedure similar to that described for DMT in Section C of Example 6.

EXAMPLE 8

OMT Injectable Formulations (A) OMT base is added to propylene glycol. Water and benzyl alcohol are added so that the solution contains 50% (by volume) propylene glycol, 4% (by volume) benzyl alcohol, and 200 mg/ml of OMT base.

(B) An OMT solution is prepared as described in Section A except that the solution contains 50 mg/ml of OMT base.

(C) An OMT solution is prepared as described in Section A except that the solution contains 350 mg/ml of OMT.

(D) An OMT solution is prepared as described in Section A except that the solution contains 500 mg/ml of OMT tartrate.

(E) An OMT suspension is prepared by adding finely ground OMT to carboxymethyl cellulose with thorough mixing so that the suspension contains 200 mg of OMT base per ml of suspension.

We claim:

1. A method for controlling Pasteurella infections which comprises administering to an infected or susceptible animal selected from cattle, sheep, pigs and fowl an amount effective for treating said Pasteurella infection of a composition comprising 5-O-mycaminosyl tylonolide or a pharmaceutically acceptable acid addition salt of 5-O-mycaminosyl tylonolide and a suitable pharmaceutical vehicle.

2. The method of claim 1 wherein the compound is 5O-mycaminosyl tylonolide.

3. The method of claim 1 wherein the compound is 5-O-mycaminosyl tylonolide tartrate.

4. The method of claim 1 wherein the compound is 5-O-mycaminosyl tylonolide phosphate.

5. The method of claim 1, 2, 3, or 4 wherein the vehicle is aqueous propylene glycol.

6. The method of claim 1, 2, 3, or 4 wherein the composition is administered as a single injection.

7. The method of claim 1, 2, 3, or 4 wherein divided doses of the composition are administered in a series of injections.

* * * * *